United States Patent
Garcia I Tormo et al.

(10) Patent No.: US 12,272,066 B2
(45) Date of Patent: Apr. 8, 2025

(54) APPARATUS, METHOD AND COMPUTER PROGRAM FOR MONITORING A SUBJECT DURING A MEDICAL IMAGING PROCEDURE

(71) Applicant: KONINKLIJKE PHILIPS N.V., Eindhoven (NL)

(72) Inventors: Albert Garcia I Tormo, Eindhoven (NL); Rink Springer, Eindhoven (NL); Ihor Olehovych Kirenko, Veldhoven (NL); Julien Senegas, Hamburg (DE); Holger Schmitt, Luetjensee (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 371 days.

(21) Appl. No.: 17/780,483

(22) PCT Filed: Dec. 1, 2020

(86) PCT No.: PCT/EP2020/083995
§ 371 (c)(1),
(2) Date: May 26, 2022

(87) PCT Pub. No.: WO2021/110613
PCT Pub. Date: Jun. 10, 2021

(65) Prior Publication Data
US 2023/0005154 A1    Jan. 5, 2023

(30) Foreign Application Priority Data
Dec. 3, 2019    (EP) ..................................... 19213100

(51) Int. Cl.
*G06T 7/11*    (2017.01)
*A61B 6/00*    (2006.01)
(Continued)

(52) U.S. Cl.
CPC .............. *G06T 7/11* (2017.01); *A61B 6/5247* (2013.01); *A61B 6/582* (2013.01); *G06T 7/73* (2017.01);
(Continued)

(58) Field of Classification Search
CPC ..... G06T 7/11; G06T 7/73; G06T 7/80; G06T 2207/30196; G06T 7/246;
(Continued)

(56) References Cited

U.S. PATENT DOCUMENTS

2007/0036413 A1\* 2/2007 Beck ...................... A61B 5/704
382/128
2008/0095416 A1   4/2008 Jeung
(Continued)

FOREIGN PATENT DOCUMENTS

| EP | 3469990 A1 \* | 4/2019 |
|----|---------------|--------|
| WO | WO2009129457 A1 | 10/2009 |
| WO | WO2018069419 A1 | 4/2018 |

OTHER PUBLICATIONS

PCT International Search Report, International application No. PCT/EP2020/083995, Feb. 4, 2021.
(Continued)

*Primary Examiner* — Samir A Ahmed
(74) *Attorney, Agent, or Firm* — Larry Liberchuk

(57) ABSTRACT

The invention refers to an apparatus for monitoring a subject (121) during an imaging procedure, e.g. CT-imaging. The apparatus (110) comprises a monitoring image providing unit (111) providing a first monitoring image and a second monitoring image acquired at different support positions, a monitoring position providing unit (112) providing a first monitoring position of a region of interest in the first monitoring image, a support position providing unit (113) providing support position data of the support positions, a (Continued)

position map providing unit (114) providing a position map mapping calibration support positions to calibration monitoring positions, and a region of interest position determination unit (115) determining a position of the region of interest in the second monitoring image based on the first monitoring position, the support position data, and the position map. This allows to determine the position of the region of interest accurately and with low computational effort.

12 Claims, 5 Drawing Sheets

(51) Int. Cl.
    *A61B 6/58*     (2024.01)
    *G06T 7/73*     (2017.01)
    *G06T 7/80*     (2017.01)
    *A61B 6/04*     (2006.01)

(52) U.S. Cl.
    CPC .............. *G06T 7/80* (2017.01); *A61B 6/0407* (2013.01); *G06T 2207/30196* (2013.01)

(58) Field of Classification Search
CPC . G06T 2207/10081; G06T 2207/30208; A61B 6/5247; A61B 6/582; A61B 6/0407; A61B 6/032; A61B 5/0035; A61B 5/1128
See application file for complete search history.

(56) References Cited

U.S. PATENT DOCUMENTS

| | | | |
|---|---|---|---|
| 2009/0285357 A1* | 11/2009 | Khamene | A61B 6/5217 378/207 |
| 2011/0154569 A1 | 6/2011 | Wiggens | |
| 2013/0114871 A1* | 5/2013 | Berkus | G06T 11/008 382/131 |
| 2018/0133518 A1* | 5/2018 | Harper | A61N 5/1049 |
| 2020/0258243 A1* | 8/2020 | Chang | A61B 5/0077 |
| 2020/0268339 A1* | 8/2020 | Hao | A61B 6/032 |

OTHER PUBLICATIONS

Heinz C. et al., "Technical Evaluation of Different Respiratory Monitoring Systems Used for 4D CT Acquisition Under Free Breathing", Journal of Applied Clinical Medical Physics, vol. 16, No. 2, pp. 334-349, 2015.

Silverstein E. et al., "Comparative Analysis of Respiratory Motion Tracking Using Microsoft Kinect v2 Sensor", Journal of Applied Clinical Medical Physics, vol. 19, No. 3, pp. 193-204, 2018.

* cited by examiner

APPARATUS, METHOD AND COMPUTER PROGRAM FOR MONITORING A SUBJECT DURING A MEDICAL IMAGING PROCEDURE

FIELD OF THE INVENTION

The invention relates to an apparatus, a method and a computer program for monitoring a subject during a medical imaging procedure. Further, the invention relates to a system for acquiring a medical image of a subject and comprising the apparatus, and an apparatus for providing a position map for being used in the apparatus.

BACKGROUND OF THE INVENTION

In many medical imaging procedures it is important to monitor a patient during the imaging procedure, for instance, to monitor movement of the patient during the procedure or to monitor the well-being of the patient during the imaging procedure, wherein monitoring images, like video images, provided by cameras, for instance, wide field of view cameras, are used for the monitoring. Moreover, for these monitoring applications it is particularly important to monitor a predetermined region of interest of the patient. For instance, if breathing motions should be monitored, the chest of the patient has to be monitored, or, if a well-being of the patient should be monitored, the face of the patient has to be monitored. Since during certain medical imaging procedures, like CT imaging procedures or MR imaging procedures, the patient may be moved through the imaging device, for monitoring the region of interest of the patient this region of the patient has to be tracked in the provided monitoring images. One of the problems in tracking a region of interest of a patient in a monitoring image when the patient is moved through a medical imaging device during a medical imaging procedure is that the shape of the region of interest will change in the monitoring image during the imaging procedure, due to the change of perspective of the monitoring camera with respect to the region of interest. This hardens purely image based tracking of a region of interest to be monitored during a medical imaging procedure. US 2008/095416 discloses a marker system in which a marker is moved from a first predetermined position to a second predetermined position. It is used for determining a position of a camera in a multi-camera system. A first camera is selected as a reference location from which the position and orientation of the other camera is based, based on the local coordinate system of the first camera. US 2011/154569 discloses a mobile patient support system. A positioning system is used for determining an actual position associated with the patient support with respect to a multi-dimensional coordinate system.

SUMMARY OF THE INVENTION

It is an object of the present invention to provide an apparatus, an imaging system comprising the apparatus, a method and a computer program that allow for an accurate and less computationally expensive monitoring of a region of interest of a subject during the acquisition of a medical image.

The invention is defined by the claims.

In a first aspect of the invention an apparatus for monitoring a subject during a medical imaging procedure using a medical imaging device is presented, wherein the imaging device comprises a support for supporting the subject and moving the subject during the imaging procedure, wherein the apparatus comprises a) a monitoring image providing unit for providing monitoring images of the subject comprising a first monitoring image and a second monitoring image of the subject, wherein the first monitoring image is acquired at a first support position and the second monitoring image is acquired at a second support position, b) a monitoring position providing unit for providing a first monitoring position and shape being indicative of a position and shape of a region of interest in the first monitoring image, c) a support position providing unit for providing support position data being indicative of the second support position, d) a position map providing unit for providing a position map, wherein the position map provides a mapping between calibration support positions and calibration monitoring positions, wherein a calibration monitoring position is indicative of a position of a calibration object in a calibration monitoring image acquired at a respective calibration support position, e) a region of interest position determination unit for determining a position and shape of the region of interest in the second monitoring image based on the first monitoring position and shape, the support position data, and the position map.

Since the region of interest position determination unit is adapted to determine a position of the region of interest in a second monitoring image based on the first monitoring position, the support position data indicative of the position of the support at which the second monitoring image of the subject was acquired, and the position map that maps calibration support positions into calibration monitoring positions, information on the position of the support at the acquisition of the second monitoring image can be taken into account for tracking a region of interest in the second monitoring image. This provides a computationally effective way of accurately tracking the region of interest during a monitoring of a subject. Moreover, since the position map is used for the determination of the region of interest in the second monitoring image, the position can be determined in a computationally effective way. Thus, the position of the region of interest in the second monitoring image can be determined accurately and with low computational effort.

The apparatus is adapted to monitor a subject during a medical imaging procedure using a medical imaging device. The medical imaging device can be, for instance, a CT system, an MR imaging system, a PET system, etc. The imaging device comprises a support, like a patient table, for supporting the subject and moving the subject during the imaging procedure. Preferably, the subject is moved by the support through the medical imaging device during the imaging procedure, for instance, through a bore of the imaging device. Alternatively, the support can also be adapted to move a subject relative to an open medical imaging device, like a C-arm CT system. The support can be an integral part of the imaging device or can be an optional part of the imaging device that can be attached or detached to and from the imaging device. The subject being imaged by the medical imaging device can be an animal or a human being. Preferably, the subject is a human patient.

The monitoring image providing unit is adapted to provide monitoring images of the subject. The monitoring image providing unit can be a storing unit on which the monitoring images are stored already and from which the monitoring images can be retrieved. Also, the monitoring image providing unit can be a retrieving unit for retrieving the monitoring images, for instance, from a monitoring camera adapted to provide the monitoring images. Preferably, the same monitoring camera is used for acquiring all monitoring images, in particular for acquiring the first and the second monitoring image. The monitoring camera can be provided as part of the imaging device and positioned, for instance, within a bore of the imaging device, or can alternatively be separate from the imaging device and positioned, for instance, in a corner of a room comprising the imaging device. In an alternative embodiment, a plurality of different camera can be used for acquiring the monitoring images of the subject. In one embodiment, a first camera can be provided at a first position relative to the medical imaging device and provide monitoring images for a first plurality of support positions and a second camera can be provided at a second position relative to the medical imaging device and provide monitoring images for a second plurality of support positions. Generally, different cameras can be used for providing monitoring images of different support positions.

The monitoring images comprise a first monitoring image and a second monitoring image. Further, the monitoring images can comprise additional monitoring images for the same or other support positions. Any monitoring image provided by the monitoring image providing unit can be defined as first monitoring image, and thus also any position of the support during the imaging procedure can be defined as the first support position. Preferably, the first support position at which the first monitoring image is acquired refers to a general starting position of the support for a medical imaging procedure. For instance, the first support position can refer to a position of the support at which the patient is prepared for the medical imaging procedure. Further, the first support position can refer to the first position of the support that allows to acquire a monitoring image of the region of interest of the patient, or to a support position at which the acquisition of the medical image is started. The first support position can, for instance, also be defined as a last position of the support during the acquisition of the medical image, as a middle position of the support during the acquisition of the medical image, etc. Any monitoring image provided by the monitoring image providing unit that is not defined as first monitoring image can be defined as second monitoring image such that any arbitrary position of the support at which the defined second monitoring image was acquired can be defined as the second support position. Preferably, if the first support position refers to a starting position of the support when starting the medical imaging, the second support position can be any of the further positions that the support assumes during the medical imaging procedure and for which a monitoring image has been acquired.

The monitoring position providing unit is adapted to provide a first monitoring position, wherein the first monitoring position is indicative of a position of a region of interest in the first monitoring image. The monitoring position providing unit can be a storing unit on which the first monitoring position is stored already and from which the first monitoring position can be retrieved. Also, the monitoring position providing unit can be a retrieving unit for retrieving the first monitoring position, for instance, from a user interface on which a user of the medical device can indicate the position of the region of interest in the first monitoring image. The first monitoring position can be a point in the first monitoring image that lies, for instance, in the middle of the region of interest. Also, the first monitoring position can be defined by a boundary around the region of interest. For instance, if the region of interest is a chest of the patient, a user interface can provide the first monitoring image to a user of the medical device, wherein the user then delineates the chest of the patient in the first monitoring image. In this example, the first monitoring position can be a point in the middle of the delineated region of interest. In other examples however, the first monitoring position can also refer to a point on the delineated contour of the region of interest, for instance, a corner of the delineated region of interest. Preferably, the monitoring position providing unit is adapted to provide more than one first monitoring positions, wherein the more than one first monitoring positions can, for instance, correspond to different positions along a boundary of the region of interest or to different corners of a bounding box surrounding the region of interest.

The monitoring position providing unit can also be adapted to automatically determine the first monitoring position based on predefined characteristics of the region of interest. For instance, if a face of a patient should be monitored the monitoring position providing unit can be adapted to use a face recognition algorithm to provide a position of the face of the subject in the first monitoring image as first monitoring position. Moreover, if the motion of a region of interest of a patient, for instance a breathing motion in a chest area of the patient, should be monitored, the monitoring image providing unit can be adapted to provide a plurality of first monitoring images, wherein each of the first monitoring images is acquired at the same support position. In this embodiment, the monitoring position providing unit can be adapted to search for a motion in the plurality of first monitoring images and to determine a region of interest based on a detected motion in the plurality of first monitoring images. Moreover, the region of interest can also be determined based on a predefined characteristic of the detected motion, for instance, on a specific motion frequency, amplitude, or sequence. The monitoring position providing unit can then be adapted to provide a position of the so determined region of interest as the first monitoring position.

The support position providing unit is adapted to provide support position data that is indicative of the second support position. The support position providing unit can be a storing unit on which the support position data is already stored and from which the support position data can be retrieved. Also, the support position providing unit can be a receiving unit for receiving the support position data, for instance, from a position sensor adapted to acquire a position of the support during the image acquisition procedure. The support position can be acquired, for instance, in a world coordinate system, like a coordinate system of the room in which the medical imaging device is provided, or can be acquired relative to another support position, for instance, the first support position. Moreover, the support position data can also be indicative of the first support position, for instance, the support position data can comprise the coordinates of the first and the second support position.

The position map providing unit is adapted to provide a position map. The position map providing unit can be a storing unit on which the position map is stored already and from which the position map can be retrieved. The position map is preferably acquired during a calibration procedure and maps calibration support positions into calibration monitoring positions. The mapping provided by the position map can refer to any kind of mapping, for instance, the mapping can comprise a mathematical function linking a calibration support position to at least one calibration monitoring position. Preferably, the mapping refers to providing a look-up table linking the calibration support positions to the calibration monitoring positions.

The position map is determined during a calibration procedure, which can be a real calibration procedure or a virtual calibration procedure. During a real calibration procedure, a real medical imaging device and a real calibration object can be used. In this embodiment, the calibration support positions refer to positions of the real support at which, during a calibration procedure for determining the position map, monitoring images, in particular calibration monitoring images, are acquired. Generally, the calibration support positions correspond to support positions that can also be assumed by the support during the acquisition of the medical imaging procedure. The calibration monitoring positions are indicative of a position of a calibration object supported by the support in a calibration monitoring image, i.e. a monitoring image acquired during a calibration procedure at a respective calibration support position. The calibration object can be specifically adapted for the calibration, i.e. for the determination of the position map. For example, the calibration object can be a box or a patient phantom that can be positioned on the support during the calibration procedure. Alternatively, the calibration object can also be an animal or a human being that is placed on the support during a calibration procedure for determining the position map.

Preferably, the calibration monitoring images in which calibration monitoring positions are determined during the calibration procedure correspond to the monitoring images provided during the medical imaging procedure. In particular, it is preferred that the calibration monitoring images comprise the same field of view as the monitoring images acquired during the medical imaging procedure, wherein this can be achieved, for instance, by acquiring the calibration monitoring images with the same camera as the monitoring images during the medical imaging procedure. Alternatively, if the calibration monitoring images are acquired using a different field of view or a different camera, a registration function can be determined for registering the calibration monitoring images with the monitoring images acquired during the medical imaging procedure and the registration function can be incorporated into the position map. The position map provides thus a link between a position of the support and a position of an object or part of an object positioned on the support in a monitoring image acquired during the medical imaging procedure. Additionally or alternatively, a common coordinate system can be defined for the monitoring images and the calibration monitoring images and the first monitoring position and the calibration monitoring positions are provided in the common coordinate system.

Alternatively, the position map can be determined during a virtual calibration procedure, wherein during the virtual calibration procedure a real calibration procedure as described above can be simulated on a general or dedicated computer system using according virtual computer models. For instance, a virtual calibration object can be chosen comprising a plurality of virtual calibration positions and the positions of the virtual calibration object in virtual or real monitoring images of the camera can be calculated, i.e. simulated, for determining the position map in accordance with the above described principles.

The region of interest position determination unit is adapted to determine a position of the region of interest in the second monitoring image based on the first monitoring position, the support position data and the position map. Thus, the region of interest position determination unit is adapted to use the information provided by the position map on where an object is positioned in the monitoring image for a certain support position, the information on an actual support position and the information on the position of the region of interest in one of the current monitoring images to determine and thus monitor the region of interest in the monitoring images acquired during the medical imaging procedure. Preferably, the region of interest position determination unit is adapted to determine a second monitoring position in the second monitoring image, wherein the second monitoring position is determined by mapping the first monitoring position in the first monitoring image to the second monitoring image using the position map. Moreover, it is then preferred that the region of interest position determination unit is adapted to determine the region of interest in the second monitoring image based on the second monitoring position. For instance, the region of interest in the second monitoring image can be defined by the same relation to the second monitoring position as the region of interest in the first monitoring image has to the first monitoring position. In a preferred embodiment, the region of interest position determination unit can be adapted to determine the region of interest in the second monitoring image based on the second monitoring position and further based on the second support position. For instance, a shape and/or size of the region of interest in the second monitoring image can be determined based on information on an expected distortion of a region of interest at the second support position. In an example, if the region of interest is defined in the first monitoring image as a rectangular region and the first monitoring position as a corner of the rectangular region, the region of interest position determination unit can determine the region of interest in the second monitoring image as a rhombic area with the second monitoring position referring to a corresponding corner of the rhombic area. Information on an expected distortion of a region of interest can be determined, for instance, during a calibration procedure and can be stored linked to a specific support position. Alternatively, the region of interest position determination unit can be adapted to determine the region of interest in the second monitoring image by registering the content of the region of interest with the second monitoring image, wherein the first and second monitoring positions provide a starting point for the registration.

In an embodiment, the monitoring images comprise a plurality of second monitoring images acquired during at least one second support position, wherein the support position providing unit is adapted to provide support position data for each of the at least one second support position and wherein the region of interest position determination unit is adapted to determine the position of the region of interest in each of the second monitoring images. Preferably, the monitoring image providing unit is adapted to provide the monitoring images in the form of a monitoring video, wherein each of the monitoring images of the video not defined as first monitoring image can be defined as second monitoring image. Each of the second monitoring images of the monitoring video can be related to a support position, for instance, by using timing information of the acquisition of the monitoring images and the acquisition of the support positions.

In a preferred embodiment, the apparatus further comprises a monitoring unit for monitoring a change in the region of interest of the subject, wherein the change is monitored based on the second monitoring images and the position of the region of interest in the second monitoring images. Since the monitoring unit is adapted to monitor changes based on second monitoring images and the position of the region of interest in the second monitoring images, the monitoring unit can very accurately distinguish between changes, like motion, that are caused by the movement of the support and changes that are caused by the subject. Thus, changes cause by the movement of the subject can be determined from the monitoring images very accurately. In an embodiment, the monitoring unit can be adapted to monitor the changes further taking the first monitoring images into account. Additionally, taking the first monitoring images into account can provide a basis for assessing measurement values in the second monitoring images. For instance, if a temperature should be monitored in the second monitoring images, the first monitoring images can provide a base value at the start of the imaging procedure with which the following temperature values determined from the second monitoring images can be compared.

Preferably, the monitoring unit is adapted to monitor as changes a motion of the subject, for instance, breathing motion, cardiac motion, motions of extremities, etc. In particular, a breathing motion of a patient can be monitored very accurately if the region of interest is defined as chest region of the patient. Alternatively, the region of interest can also be any other part of the patient in which motion has to be detected very accurately. In another example, the region of interest of the patient can be a face of the patient, wherein the apparatus can further comprise a monitoring unit for monitoring motions in the face of the patient based on the second monitoring images and the position of the region of interest in the second monitoring images to determine, for instance, a state of the patient, like if the patient is asleep or awake, or if the patient is stressed or relaxed, etc. Additionally or alternatively to monitoring changes caused by motion of the subject, also other changes can be monitored, like changes in a temperature of the patient, changes in the skin tone of the patient, etc. For instance, this monitoring can be helpful for monitoring a wellbeing of a patient, like when the patient skin turns pale, this can indicate cardiac or circulatory problems, for example, caused by stress or panic. Moreover, the cardiac motion can be monitored using, for instance, the face of a patient, wherein in this case color changes, in particular, changes of the skin tone of the patient, in the monitored region of interest are monitored that are indicative of the blood flow and thus of cardiac processes and cardiac motion.

In an embodiment, the position map maps to each calibration support position a plurality of calibration monitoring positions, each calibration monitoring position being indicative of a position of a different part of the calibration object. For instance, if the calibration object is a real or virtual calibration box, the calibration monitoring positions can correspond to the positions of the corners of the calibration box in the calibration monitoring images. In a preferred embodiment, the real or virtual calibration object is a box comprising a checkerboard pattern, wherein the position map maps to each calibration support position the positions of the corners of each field of the checkerboard pattern in the respective calibration monitoring image as calibration monitoring positions. Providing more than one calibration monitoring position for each calibration support position in the position map allows to monitor the region of interest in the monitoring images more accurately.

In an embodiment, the first region of interest providing unit is adapted to provide a first monitoring position in the first monitoring image that corresponds to a calibration monitoring position in one of the calibration monitoring images. For instance, the first monitoring image can be provided by a user interface to a user and the user interface can be adapted to only allow the user to select a first monitoring position in the first monitoring image that corresponds to one of the calibration monitoring positions in the position map. Alternatively, determining the position of the region of interest in the second monitoring image comprises determining a first calibration monitoring position, wherein the first calibration monitoring position corresponds to a calibration monitoring position in the position map that is derived from the first monitoring position in the first monitoring image, wherein determining the position of the region of interest is further based on the first calibration monitoring position. Preferably, the first monitoring position is derived from the first monitoring position by searching for a calibration monitoring position that lies in the proximity of the first monitoring position, wherein the proximity which is searched can be predetermined. For instance, it can be predetermined that first it is determined if a calibration monitoring position lies within a first proximity threshold, for instance, within a first radius around the first monitoring position. If none is found within the first proximity threshold, it is searched for a calibration monitoring position within a second proximity threshold, and so on, until a calibration monitoring position is found that is then determined as the first calibration monitoring position. Alternatively, the calibration monitoring position nearest to the first monitoring position is derived as the first calibration monitoring position. The nearest calibration monitoring position can be determined, for instance, by determining a Euclidian distance between the first monitoring position and all calibration monitoring positions provided by the position map, wherein the nearest calibration monitoring position is the calibration monitoring position with the smallest Euclidean distance to the first monitoring position. Also other distance measures can be used for determining a nearest calibration monitoring position as first calibration monitoring position. Moreover, the distance between the first calibration monitoring position and the first monitoring position, and/or the difference between the first calibration monitoring position and the first monitoring position, for instance, with respect to an x- and y-coordinate of the positions in the monitoring images, can be stored. The region of interest position determination unit can then also be adapted to use this stored difference together with the first calibration monitoring position to determine the position of the region of interest. This allows a very accurate determination of the position of the region of interest in the second monitoring image with only a few calibration monitoring positions.

In an embodiment, determining the position of the region of interest in the second monitoring image comprises determining at least two calibration monitoring positions that are derived from the first monitoring position as first calibration monitoring positions, wherein the position of the region of interest is then determined further by interpolating between monitoring positions determined in the second monitoring image based on the position map and the first calibration monitoring positions. The at least two first calibration monitoring positions can be derived, for instance, by defining all or a part of the calibration monitoring positions within a proximity of the first monitoring position as first calibration monitoring position. For example, the proximity can be predefined as an area around the first calibration monitoring position, wherein then all calibration monitoring positions in this area are defined as first calibration monitoring positions. Additionally or alternatively, the calibration monitoring positions nearest the first monitoring positions can be defined as first calibration monitoring positions. If more than one first calibration monitoring position should be determined from a plurality of calibration monitoring positions, the nearest first calibration monitoring positions refer to the nearest calibration monitoring position, the second nearest calibration monitoring position, the third nearest calibration monitoring position, etc., until a predetermined number of nearest calibration monitoring positions is reached. In a preferred example, the calibration monitoring positions are uniformly spaced in at least a part of a calibration monitoring image of a calibration support position. In this case, it is preferred that as first calibration monitoring positions calibration monitoring positions are determined corresponding to the corners of a square surrounding the first monitoring position. From the first calibration monitoring positions and the position map, monitoring positions for each of the first calibration monitoring positions can be determined in the second monitoring image. By interpolating between the so-determined monitoring positions, the position of the region of interest in the second monitoring image can be determined very accurately.

In an embodiment, determining the position of the region of interest in the second monitoring image comprises determining a virtual first support position based on the first monitoring position and the position map, and determining the position of the region of interest in the second monitoring image based on the virtual first support position, the support position data and the position map. The virtual first support position can be determined, for instance, by mapping the first monitoring position, using the position map, into a support position. The virtual first support position thus does not necessarily correspond to the first support position. For instance, if the calibration monitoring positions of the position map are determined based on a calibration object positioned at the middle of the support, whereas the first monitoring position of the region of interest is determined at one end of the support, the position map will provide, as virtual first support position, a position differing from the first support position. An accurate position of the region of interest can then be determined based on the virtual first support position. For instance, in such a case a difference between the second support position and the first support position included in the support position data can be determined and the position of the region of interest in the second monitoring image can be determined based on this difference and the virtual first support position from the position map. Preferably, the support position data comprises a difference between the first support position and the second support position, and the region of interest position determination unit is adapted to determine the position of the region of interest in the second monitoring image based on the first monitoring position, the difference, and the position map.

In an embodiment, the support position providing unit is adapted to provide the support position data based on the first monitoring image and the second monitoring image by identifying the support in the respective monitoring images. For instance, the support position providing unit can be adapted to provide the support position data based on the monitoring images by tracking the support in the monitoring images based on a known object tracker algorithm or a marker provided on the support of the imaging device. In both cases the support can be easily tracked in the monitoring images with very small computational effort. Providing the support position data based on the monitoring images allows to directly relate each monitoring image to a support position without providing additional hardware like a support position sensor.

In an embodiment, each monitoring image is acquired by the same camera, wherein the field of view of each monitoring image is the same and covers all positions of interest of the region of interest during the medical imaging procedure. Preferably, the camera is attached to the medical imaging device. Alternatively, the camera can be provided independent of the medical imaging device, for instance, on a ceiling or a corner of a room comprising the medical imaging device. Further, it is preferred that the calibration monitoring images are acquired using the same camera with the same field of view. In one embodiment the camera can be a wide field of view camera.

In an alternative embodiment, the monitoring images are acquired by at least two cameras with different fields of view, wherein the different fields of view may overlap to allow monitoring the complete medical imaging procedure. Preferably, the cameras are attached to the medical imaging device. Alternatively, the cameras can be provided independent of the medical imaging device, for instance, on a ceiling or a corner of a room comprising the medical imaging device. Further, it is preferred that the calibration monitoring images are acquired using the same cameras at the same positions as used during the monitoring.

In an aspect of the invention, a calibration apparatus for providing a position map for being used in an apparatus defined above is presented (as well as the apparatus defined above which further comprises the calibration apparatus), wherein the apparatus comprises a) a calibration monitoring image providing unit for providing calibration monitoring images, wherein each calibration monitoring image is acquired at a different calibration support position and is indicative of the position of a calibration object supported by the support, b) a calibration support position providing unit for providing calibration support position data, wherein the calibration support position data is indicative of the support positions during the calibration, and c) a position map determination unit for determining a position map by determining a mapping between the positions of the calibration object and the respective calibration support position for each calibration monitoring image.

The calibration monitoring image providing unit can be a storing unit on which the calibration monitoring images are already stored and from which the calibration monitoring images can be retrieved. Also, the calibration monitoring providing unit can be a retrieving unit for retrieving the calibration monitoring images, for instance, from a monitoring camera that should be used for monitoring a subject during a medical imaging procedure. Preferably, each calibration monitoring image has the same field of view as a monitoring image acquired during a medical imaging procedure at the same support position. In such a calibration procedure a calibration object is provided on the support of the medical device and monitored by the camera to provide the calibration monitoring images. The calibration object can be, for instance, a dedicated calibration object, preferably a cube comprising a checkerboard pattern, a phantom or a human being.

The calibration support position providing unit is adapted to provide calibration support position data indicative of the position of the support during the calibration procedure. The calibration support position providing unit can also be a storing unit in which the calibration support position data is already stored and from which the calibration support position data can be retrieved. Also, the calibration support position providing unit can be a receiving unit for receiving the calibration support position data, for instance, from a position sensor of the support of the medical device or, as explained already above, from the monitoring images, for instance, the calibration monitoring images.

The position map determination unit is then adapted to determine the position map by determining a mapping between the positions of the calibration object and the respective calibration support position for each calibration monitoring image. For instance, the position map determination unit can be adapted to provide as position map a table linking each calibration support position to a position of the calibration object in the corresponding calibration monitoring image. Preferably, the position map determination unit is adapted to determine a mapping between a calibration support position and more than one position of the calibration object in the respective calibration monitoring image, wherein each position of the calibration object refers to a position of a different part of the calibration object in the calibration monitoring image. For instance, if the calibration object comprises a checkerboard pattern, the position map determination unit can be adapted to map to each calibration support position the position of each corner of each checkerboard field of the calibration object in the corresponding calibration monitoring image.

In an aspect of the invention, a system for acquiring a medical image of a subject during a medical imaging procedure using a medical imaging device is presented, wherein the system comprises a) a medical imaging device for acquiring a medical image, wherein the medical imaging device comprises a support for supporting the patient during the medical imaging procedure, b) a camera for acquiring monitoring images of the subject during the medical imaging procedure, and c) an apparatus as described above.

In a further aspect of the invention, a method for monitoring a subject during a medical imaging procedure using a medical imaging device is presented, wherein the imaging device comprises a support for supporting the subject and moving the subject during the imaging procedure, wherein the method comprises a) providing monitoring images of the subject comprising a first monitoring image and a second monitoring image of the subject, wherein the first monitoring image is acquired at a first support position and the second monitoring image is acquired at a second support position, b) providing a first monitoring position and shape being indicative of a position and shape of a region of interest in the first monitoring image, c) providing support position data being indicative of the second support position, d) providing a position map, wherein the position map provides a mapping between calibration support positions and calibration monitoring positions, wherein a calibration monitoring position is indicative of a position of a calibration object in a monitoring image acquired at a respective calibration support position, and e) determining a position and shape of the region of interest in the second monitoring image based on the first monitoring position and shape, the support position data, and the position map.

In another aspect of the invention a computer program for monitoring a subject during a medical imaging procedure using a medical imaging device is presented, wherein the computer program comprises program code means for causing the apparatus as described above to carry out the steps of the method as described above when the computer program is executed by the apparatus.

It shall be understood that the apparatus, the method, and the computer program of the invention have similar and/or identical preferred embodiments, in particular, as defined in the dependent claims.

It shall be understood that a preferred embodiment of the present invention can also be any combination of the dependent claims or above embodiments with the respective independent claims.

These and other aspects of the invention will be apparent from and elucidated with reference to the embodiments described hereinafter.

DETAILED DESCRIPTION OF EMBODIMENTS

Figure 1:
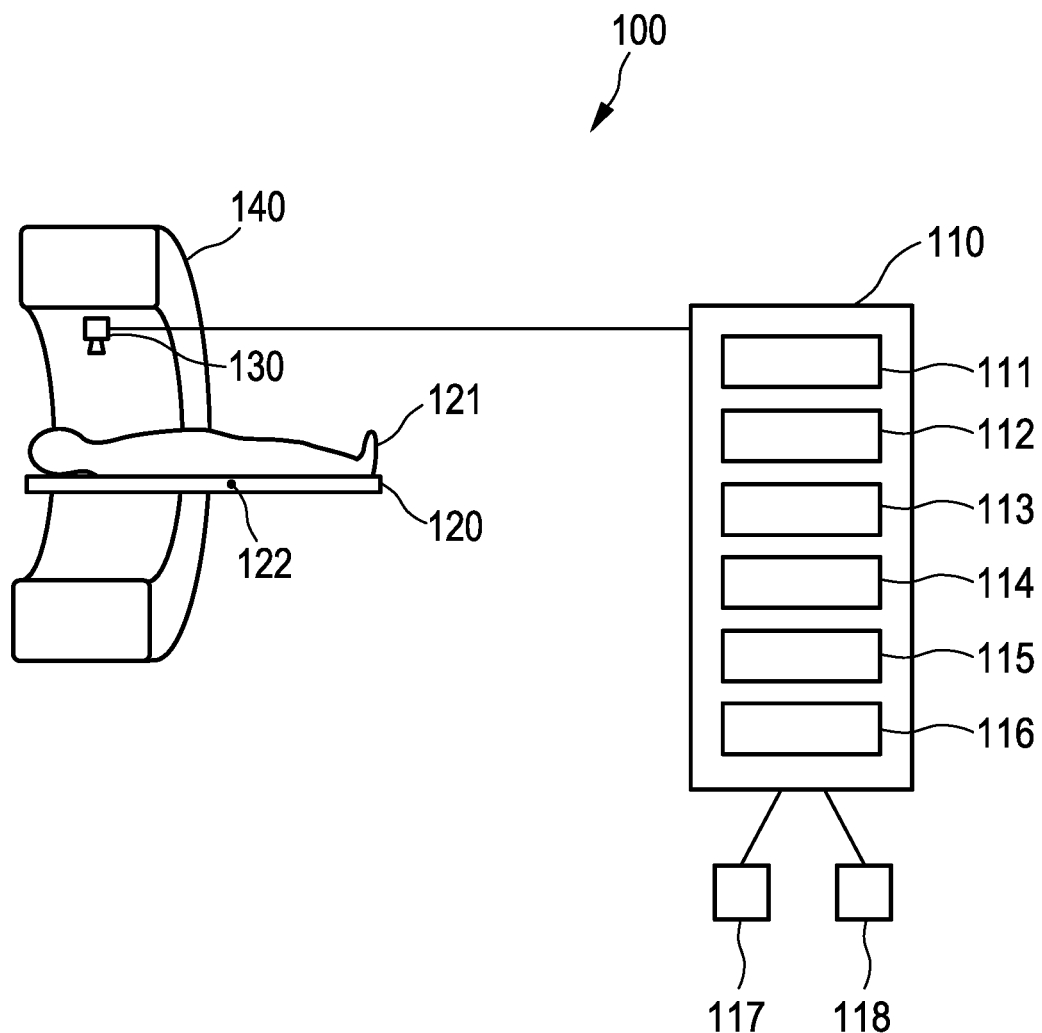
FIG. 1 shows schematically and exemplarily an embodiment of a system for acquiring a medical image of a subject comprising an apparatus for monitoring a subject during the medical imaging procedure.

FIG. 1 shows schematically and exemplarily an embodiment of a system for acquiring a medical image of a subject comprising an apparatus for monitoring a subject during the medical imaging procedure. In the following embodiment, the system 100 comprises as medical imaging device a CT system 140 that is adapted to acquire a CT image of a patient 121 being positioned on a patient support 120. The patient support 120 is adapted to move the patient 121 through the CT imaging system 140 during the CT imaging procedure. Further, the CT imaging system comprises a camera 130, as an example of a system arranged to obtain the monitoring images provided to the monitoring image providing unit, that is adapted to acquire monitoring images of the patient 121 during the CT imaging procedure. Moreover, the system 100 comprises an apparatus 110 that is adapted to process the acquired monitoring images and derive physiological parameters for monitoring the patient 121 during the acquisition of the CT image.

The apparatus 110 comprises a monitoring image providing unit 111, a monitoring position providing unit 112, a support position providing unit 113, a position map providing unit 114 and a region of interest position determination unit 115. In this embodiment, the apparatus 110 optionally comprises a monitoring unit 116. Further, the apparatus 110 can comprise input means 118, like a mouse, a keyboard or a touch screen, to input data into the apparatus 110, and output means 117, like a display, for outputting monitoring images for monitoring the patient.

The monitoring image providing unit 111 is configured as a receiving unit for receiving monitoring images of the patient 121 from camera 130. The camera 130 can be a wide field of view camera that can image the whole medical image acquisition procedure. It is preferred that the camera 130 is positioned and adapted such that the patient is within the field of view of the camera during the whole medical imaging procedure, in particular, without moving the camera or changing the position of the camera. The monitoring images of the patient 121 comprise a first monitoring image and a plurality of second monitoring images of the patient 121, wherein the first monitoring image is acquired at a first support position and the plurality of second monitoring images is acquired at different second support positions.

Preferably, the camera 130 provides a video stream, wherein each image of the video stream provided by camera 130 can then be regarded as being a monitoring image. The first monitoring image can be any of the provided monitoring images of the patient 121, but preferably refers to the monitoring image provided by camera 130 that first shows the region of interest of the patient 121 that should be monitored. In this case, all images provided by the camera 130 after the first monitoring image can be defined as second monitoring images of the patient 121. Alternatively, only a selection of the monitoring images provided by the camera 130 after the provision of the first monitoring image can be defined as second monitoring images of the patient 121. For instance, for each support position only one monitoring image can be selected as second monitoring image of the patient 121.

The monitoring position providing unit 112 is adapted to provide a first monitoring position being indicative of a position of a region of interest in the first monitoring image. Preferably, for providing the first monitoring position, the monitoring position providing unit 112 is adapted to display the first monitoring image on the display 117 and to receive the first monitoring position as input from the user. For instance, the user can mark the chest of patient 121 as region of interest by drawing, using the input means 118, a box over the chest region of the patient 121 on the first monitoring image displayed on display 117. The corners of the box drawn by the user can then be regarded as first monitoring positions defining the region of interest to be monitored. Alternatively, the first monitoring position can also be provided by the first monitoring providing unit based, for instance, on information on where the location of the region of interest is normally to be expected in the first monitoring image. In such an embodiment, the first monitoring position is preferably determined by the monitoring position providing unit based on patient data, like height, age, weight, etc. of the patient, and/or configuration data, like the height and starting position of the support 120 and a spatial relation between the camera 130 and the support 120. Based on such data, it can be estimated where a region of interest, for instance, a chest region, of a patient 120 can be found in the first monitoring image, and the monitoring position providing unit 112 can be adapted to provide the first monitoring position based on this estimation.

The support position providing unit 113 is adapted to provide support position data being indicative of the plurality of second support positions. In this embodiment, the support 120 comprises a support marker 122 and the support position providing unit is adapted to provide the support position data based on a tracking of the support marker 122 in the monitoring images of camera 130. In alternative embodiments, also a support position sensor can be provided as part of the support 120 or as part of the imaging device 140 for measuring the position of the support and providing the support positions to the support position providing unit. In this case, the support position providing unit can be adapted to determine from the provided support positions which support positions correlate to second monitoring images as provided by the monitoring image providing unit, and to provide the so-determined support positions as second support positions. The determination can be based, for instance, on time stamps of the support position data and the provided monitoring images.

The position map providing unit 114 is adapted to provide a position map. The position map provides a mapping between calibration support positions and calibration monitoring positions, wherein the calibration monitoring positions are indicative of positions of a calibration object in a monitoring image acquired during a calibration procedure at respective calibration support positions. The position map can be acquired, for instance, using a calibration system as shown in FIG. 2.

Figure 2:
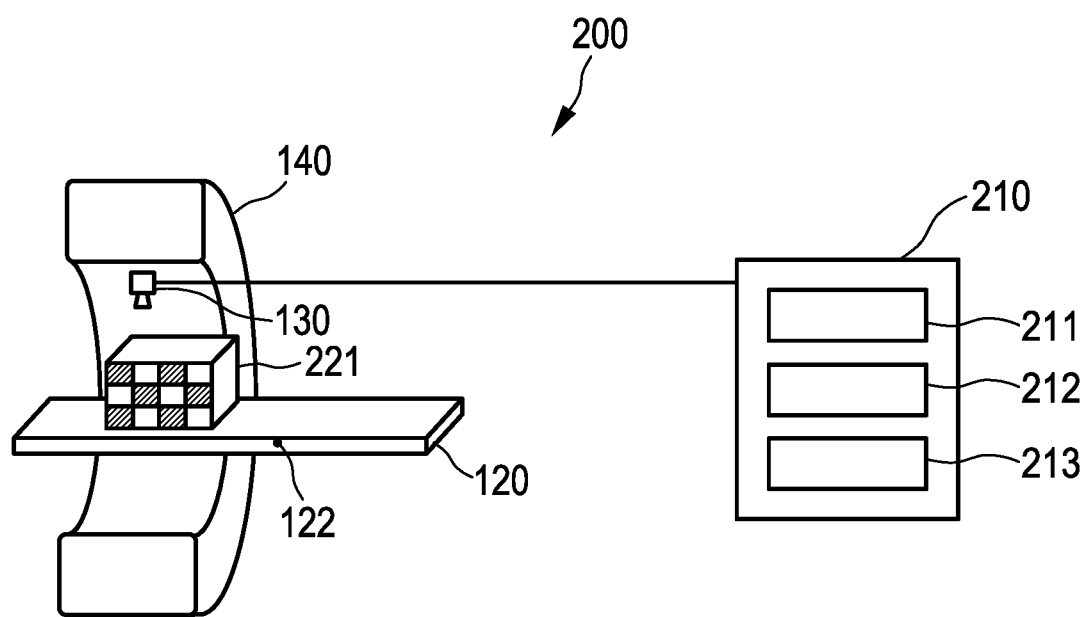
FIG. 2 shows schematically and exemplarily a system comprising an apparatus for providing a position map of the invention.

FIG. 2 shows schematically and exemplarily a system comprising an apparatus for providing a position map being used in the apparatus 110. The calibration system 200 comprises the imaging device 140, the support 120 and the camera 130 as already described with respect to FIG. 1. During the calibration procedure, instead of the patient 121 a calibration object 221 is placed on support 120, preferably in a part of support 120 in which a region of interest of the patient 121 is expected to be placed during an imaging procedure. The calibration object 221 can be a box comprising markings, for instance, in the form of a checkerboard with alternating black and white areas. In other embodiments, also other forms can be chosen for the calibration object 221, for instance, medical phantoms of patients or of part of patients can be used.

The calibration system 200 further comprises the calibration apparatus 210 comprising a calibration monitoring image providing unit 211, a calibration support position providing unit 212 and a position map determination unit 213. The calibration monitoring image providing unit 211 is adapted to provide calibration monitoring images. The calibration monitoring images correspond to monitoring images provided by camera 130 during the medical imaging procedure. Preferably, the providing of the calibration monitoring images comprises selecting, from the monitoring images provided by camera 130 during the calibration procedure, the calibration monitoring images such that each calibration monitoring image is acquired at a different support position of the support 120 during the calibration procedure, i.e. at a different calibration support position.

The calibration support position providing unit 112 is adapted to provide calibration support position data being indicative of the support positions during the calibration. In the embodiment shown in FIG. 2, the calibration support position providing unit is adapted to provide the calibration support position data based on a tracking of the support marker 122 in the monitoring images provided by camera 130. As already described above, if a support position sensor is provided, the calibration support position providing unit 112 can also be adapted to provide the calibration support position data based on the measurements of the support position sensor.

The position map determination unit 213 is adapted to determine a position map by determining a mapping between positions of the calibration object 221 and the respective calibration support positions for each calibration monitoring image. Preferably, the position map determination unit 213 is adapted to automatically determine the positions of the calibration object by recognizing different parts of the calibration object 221 in the calibration monitoring images using, for instance, known object recognition or tracking algorithms. In the embodiment shown in FIG. 2, the position map determination unit 213 can, for instance, be adapted to recognize the checkerboard pattern on the calibration object 221 and to determine as positions of the calibration object 221 the corners of each checkerboard tile. Alternatively, the position map determination unit 213 can be adapted to present the calibration monitoring images to a user, wherein the user can then indicate the calibration positions, i.e. the positions of the object, on the calibration monitoring images. Thus, for each calibration monitoring image the position map determination unit 213 can determine a plurality of positions of the calibration object 221. The position map determination unit 213 can then be adapted to map this plurality of positions of the calibration object 221 in a calibration monitoring image to the calibration support positions of the support 120 at which the calibration monitoring image has been acquired. The position map can then be determined as being a list or table sorting the positions of the calibration object 221 to the respective calibration support positions. In other embodiments, the position map determination unit 213 can be adapted to determine a function between the positions of the calibration object 221 and the respective calibration support positions, wherein in this case the position map refers to the determined function. After the calibration procedure has been performed using the calibration system 200, the position map can be stored and used in an imaging procedure for imaging, for instance, the patient 121. The position map providing unit 114 of the system 100 in FIG. 1 is then adapted to provide the stored position map acquired using the calibration system 200.

The region of interest position determination unit 115 is adapted to determine a position of the region of interest of the patient 121 in the second monitoring images provided by the monitoring image providing unit 111 based on the first monitoring position provided by the monitoring position providing unit 112, the support position data provided by the support position providing unit 113 and the position map provided by the position map providing unit 114. A preferred embodiment of the determination of the position of the region of interest in the second monitoring images will be described in the following with respect to FIG. 3.

Figure 3:
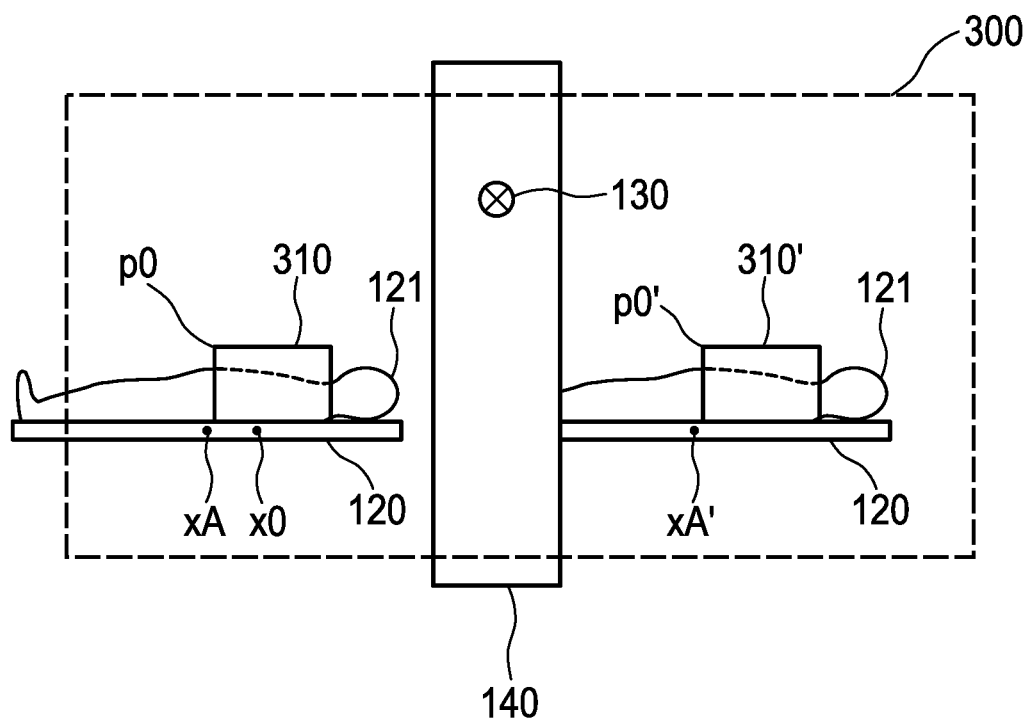
FIG. 3 shows schematically and exemplarily principles of the present invention.

FIG. 3 shows schematically and exemplarily principles of the present invention. Components that refer to components also shown in FIGS. 1 and 2 are identified by the same reference numerals. For instance, FIG. 3 also shows the imaging device 140, the camera 130, the patient 121 and the patient support 120. Further, FIG. 3 shows schematically the field of view 300 of the camera 130 during an imaging procedure. In the field of view 300, two drawings of the patient 121 and the patient support 120 are provided referring each to a different monitoring image and a different support position during the acquisition of the medical image. In particular, the left drawing of the patient 121 and the support 120 indicates where a patient 121 might be shown in a first monitoring image, and the right drawing of the patient 121 and the support 120 indicates where a patient 121 might be shown in one of the second monitoring images. The box 310 shown in the left drawing of the patient is then indicative of a region of interest that is to be monitored. In this example, the left upper corner is provided as first monitoring position p0. The actual support position at which this first monitoring image has been acquired is indicated by point xA. In this example, the region of interest position determination unit is adapted to determine a virtual first support position x0 based on the first monitoring position p0 and the position map mt. In particular, the virtual first support position x0 can be determined by applying the position map to the first monitoring position p0, such that x0=mt(p0). For instance, if the position map refers to a list, the region of interest position determination unit can be adapted to search in the entries of the list for a calibration monitoring position corresponding to the first monitoring position p0 and to provide as virtual first support position x0 the calibration support position indicated by the list as corresponding to the found calibration monitoring position.

Determining a virtual first support position x0 has the advantage that also in cases in which, during the calibration procedure, the calibration object 221 was not positioned in the same region of the support as the region of interest that should be monitored, the region of interest can be monitored very accurately based on the virtual first support position as shown in the following. In this example, the region of interest position determination unit 115 is then adapted to determine the position p0' of the region of interest in the second monitoring image, which was acquired with the patient support 120 at the actually second support position xA'. For instance, the region of interest position determination unit 115 can be adapted to determine from support position data comprising the first support position xA and the second support position xA' a difference between these two support positions, i.e. to determine Δx=xA'−xA. Alternatively, the support position data provided by the support position providing unit 113 can already comprise support position data being indicative of the difference Δx as second support position data. The region of interest position determination unit 115 can then be adapted to determine the region of interest position p0', i.e. the second monitoring position, by applying the inverse of the position map to a sum of the virtual first support position x0 and the difference Δx, i.e. p0'=mt$^{-1}$(x0+Δx). The term mt$^{-1}$ in the provided formula indicates a reversal of the search in the position map. When the region of interest position determination unit 115 has determined the second monitoring position p0' of the region of interest, further also the bounding box 310' of the region of interest in the second monitoring image can be provided. For instance, if no strong distortion is expected for the second monitoring image compared with the first monitoring image, due to the specifics of the camera, or due to only a very small difference Δx, the bounding box can be simply copied from the first monitoring image with p0' as starting point. However, if due to the specifics of the camera or a large difference Δx a change of perspective is expected, the size and shape of the bounding box marking the region of interest can be adapted in accordance with the expected distortion of the region of interest due to the change of perspective. For instance, size and shape changes of a region of interest can be predetermined during the same calibration procedure for providing the calibration map and then stored with respect to the second support positions as part of the calibration map or independent of the calibration map as additional information. Alternatively, functions can be known from theoretical considerations or from computational simulations that describe the distortion of a shape within the camera field of view and the respective functions can be applied to the bounding box marking the region of interest to determine the region of interest in the second monitoring image.

In other embodiments, the region of interest position determination unit 115 can also be adapted to determine the position of the region of interest in the second monitoring image based on other methods, for instance, without calculating a virtual first support position. In such an embodiment, the monitoring position providing unit can be adapted to determine, for instance, based on an input of the region of interest of the user, a calibration monitoring position that corresponds or is as near as possible to the input of the user and provide this calibration monitoring position as the first monitoring position. For instance, the monitoring position providing unit can be adapted to search the calibration monitoring positions in the position map for a calibration monitoring position that corresponds to an indicated position of a region of interest at the same support position. In such a case, determining a virtual first support position can be omitted. Moreover, to increase the accuracy of the determined position of the region of interest, the region of interest position determination unit 115 can be adapted to determine calibration monitoring positions in the position map that are derived from the first monitoring position, for example, if the first monitoring position lies between the corners of one of the checkerboard tiles of the calibration object 221 used as calibration monitoring positions these four corners can be derived as first calibration monitoring positions. To determine the position of the region of interest, the region of interest position determination unit 115 can then be adapted to interpolate between the positions determined for the first calibration monitoring positions in the second monitoring image. A preferred possibility for determining the first calibration monitoring positions of a first monitoring position is determining the nearest neighbors of the first monitoring position in the position map.

Based on the position of the region of interest determined in a plurality of second monitoring images, the monitoring unit 116 is adapted based on the acquired monitoring images to derive physiological parameters, such as respiration rate, enabling to for example monitor a breathing motion of the subject in the region of interest, for instance, by tracking an up and down movement in the determined region of interest. Additionally or alternatively, the monitoring unit 116 can also be adapted to monitor other motions of the patient 121 or a well-being of the patient 121. If the monitoring unit 116 is adapted to monitor the well-being of the patient 121, for instance, the face of the patient 121 can be defined as region of interest and the monitoring unit 116 can be adapted to determine the well-being of the patient 121 based on the second monitoring images and the position of the face in the second monitoring images, for instance, by monitoring movements of the face, changes in the expression of the face of a patient, temperature changes of parts of the face, or a skin tone of the skin of the face.

Figure 4:
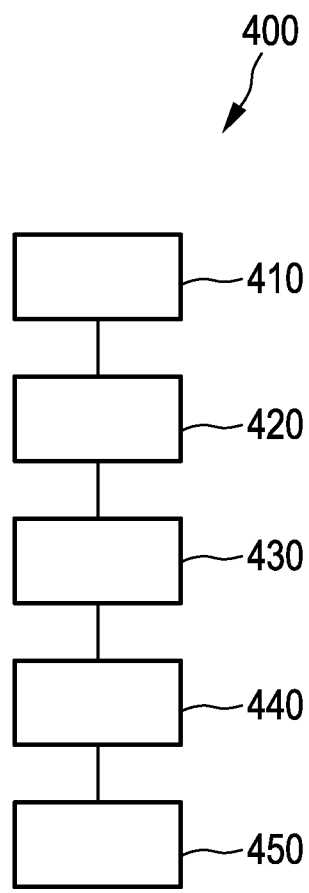
FIG. 4 shows a flow chart exemplarily illustrating an embodiment of a method for monitoring a subject during a medical imaging procedure.

FIG. 4 shows a flow chart exemplarily illustrating an embodiment of a method for monitoring a subject during a medical imaging procedure. A method 400 for monitoring a subject according to the principles of the invention as already described above comprises a first step 410 of providing monitoring images of the subject comprising the first monitoring image and the second monitoring image of the patient 121. The first monitoring image and the second monitoring image can be acquired by a camera 130. Moreover, the first monitoring image is acquired at a first support position of the patient support 120 and the second monitoring image is acquired at a second support position of the patient support 120. Further, the method comprises a step 420 of providing a first monitoring position being indicative of a position of a region of interest in the first monitoring image. The first monitoring position can be provided, for instance, by a user on a display showing the first monitoring image or can also be provided automatically by recognizing the region of interest that should be monitored. For instance, if a breathing motion should be monitored, a plurality of first monitoring images can be provided that are all acquired at the first support position, and the first monitoring position can be automatically determined by determining a region in the first monitoring image that shows the most movement. Alternatively, if the well-being of a patient should be monitored, the first monitoring position can be determined automatically by applying face recognition algorithms to the first monitoring image. Further, the method 400 comprises a step 430 of providing support position data being indicative of the second support position. For instance, the support position data can be provided based on a tracking of the marker 122 in the monitoring images provided by a camera 130.

Further, the method 400 comprises a step 440 of providing a position map, as described above with respect to FIGS. 1 and 2. The position map can be determined, for instance, based on a calibration method 500 as described below with respect to FIG. 5. The method 400 then comprises a step 450 of determining a position of the region of interest in the second monitoring image based on the first monitoring position, the support position data and the position map in accordance with the principles explained above.

Figure 5:
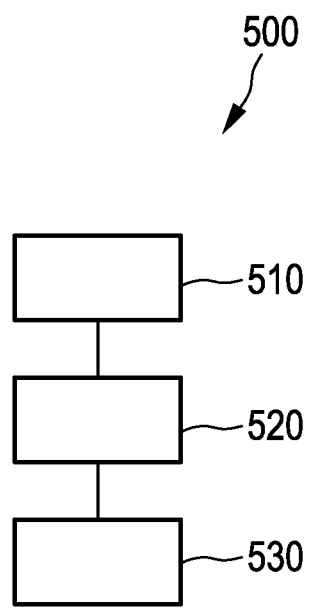
FIG. 5 shows a flow chart exemplarily illustrating an embodiment of a method for providing a position map for being used with an apparatus for monitoring a subject.

FIG. 5 shows a flow chart exemplarily illustrating an embodiment of a method for providing a position map for being used with an apparatus for monitoring a subject. The method 500 for providing a position map for being used in a method as described above for monitoring a subject comprises a first step 510 of providing calibration monitoring images, wherein each calibration monitoring image is acquired at a different calibration support position and is indicative of the position of a calibration object supported by the support. Further, the method 500 comprises a step 520 of providing calibration support position data, wherein the calibration support position data is indicative of the calibration support positions during the calibration. In step 530, the method 500 then comprises determining a position map by determining a mapping between the positions of the calibration object and the respective calibration support positions for each calibration monitoring image, for instance, as explained with respect to the calibration apparatus 210.

Medical imaging technologies, such as CT or MR, capture multiple imaging data of the patient which are subsequently combined to reconstruct the final scan images. An examination may last several seconds or even minutes, wherein during this time period the patient is asked to stay as still as possible, sometimes even to hold the breath, so that all images are taken in the most similar conditions possible and thus the final scan images are sharp and artefact-free. For instance, if a three-dimensional scan image of the chest of a patient is to be obtained with a CT examination, projection data acquired from different angles are combined, wherein if all projection data were acquired instantaneously and at once, all data would represent the patient in exactly the same position and therefore the combination of projection data would yield sharp and accurate scan images.

However, an examination lasts several seconds or minutes and during this time the patient is likely to move, even involuntarily, e.g. due to breathing or heart beating, which degrades the quality of the final reconstructed scan images. Certainly, if imaging data obtained at the moment of maximum exhalation are combined with imaging data obtained at the moment of maximum inhalation, the reconstructed scan images are blurred or contain artefacts as the shape of the patient has changed. Even if asking the patient to hold the breath, not all patients are able to stay still and hold the breath for as long as the examination takes place. In such situations, a certain degree of image-quality degradation has to be accepted.

In order to prevent degrading the image quality because of the breathing-induced movement, state-of-the-art medical imaging systems monitor the respiration of the patient and adapt the examination accordingly, for example, by attaching a measuring belt to the patient's chest. But, attaching sensors causes a certain level of discomfort to the patient and it requires a trained person to attach and remove the sensors, thereby increasing the total examination time and cost. In case the sensor is not properly attached, the resulting breathing signal is degraded and cannot be used during the examination. This leads to image quality degradation or significant time loss.

As an alternative to contact sensors, camera-based contactless respiration monitoring solutions have been proposed and successfully applied to certain medical imaging modalities such as MR imaging. State-of-the-art camera-based contactless respiration monitoring solutions measure the patient's breathing signal by tracking breathing-induced movements in the chest area, in particular, the recurrent expansion and contraction of the chest at every breathing cycle. Such algorithms require the patient to stay still, such that no motion is superimposed over the breathing-induced motion.

In some imaging technologies, such as CT or MR, the patient lies on a patient support, also referred to as table or couch, and the patient support is moved through the CT gantry aperture during a CT imaging procedure or the MR imaging gantry during an MR imaging procedure. The patient support may be moved in steps, and imaging data can be acquired during no-motion periods, wherein this technique is known as "step and shoot", or the patient support may be continuously moved whilst images are being acquired, wherein this technique is used in particular during helical CT scans. In either case, continuous respiration monitoring based on a fixed camera is not feasible with state-of-the-art respiration algorithms, as they require the patient not to move within the camera's field of view, i.e. no translation movement is allowed to be superimposed on the breathing signal. From the camera standpoint, the translation movement masks the breathing-induced movement, wherein the movement of the support is much larger and thus the camera-monitoring algorithm is not able to isolate the breathing signal.

Also a simple automatic image based tracking of a chest area of the patient is not possible. The chest area where the breathing signal can be measured may have a substantially different shape from patient to patient, making it difficult for automatic image based tracking algorithms to automatically identify the chest area from different perspectives. Even if the chest area is manually selected for each patient, the perspective on the chest changes whilst the examination takes place as a result of the support motion, i.e. the object to be tracked morphs into a different object during tracking. Nowadays it is not possible to accurately track an object under such circumstances based on images of the object, and therefore relying on an object tracking algorithm to identify the chest is not a feasible method for identifying the translation movement.

The present invention provides a method and a system that allow monitoring a region of interest, like the chest, on a monitoring image by using additional information about the support position. The tracking of the region of interest can then be used to isolate, for instance, the breathing signal from the translation signal. In particular, it is proposed to determine an initial one-time calibration, i.e. a calibration map, and to use this calibration during the tracking.

In an embodiment, the system according to the principles of the invention can comprise, for instance, a medical imaging device, a camera which is fixed to the medical imaging device or fixed in the room, a patient support or patient table, preferably including positioning sensors which indicate the exact patient support position at which a patient lies at any time, and which moves a patient through the medical imaging device, a control system of the medical imaging device, which can provide a signal indicating the exact patient support position at any time, and a processing unit, for instance, the apparatus described above, which combines the information captured by the camera, for instance, in a video stream, and the patient support position signal, and provides the patient's breathing signal. Preferably, the medical imaging device is equipped with a camera with a lens with a wide field of view, typically a fisheye lens. The camera can be fixed to the medical imaging device and, from its fixed position, the chest of the patient should be visible in all patient support positions of interest. Alternatively, the camera may be fixed in the room or can be provided on a tripod near the medical imaging device.

In an embodiment of the invention, a method according to the principles of the invention can consist in performing an initial calibration based on an easily identifiable object, i.e. a calibration object, and creating a position map. This position map can determine, for each patient support position, which positions, for instance, pixels in the video image, i.e. monitoring image, correspond to the calibration object that is positioned on the patient support. Relying on this position map it is possible to track, in the video stream, i.e. in the monitoring image, any object lying on the patient support during a support motion by simply identifying the object once, for instance, before motion starts, and then analyzing the support position. Preferably, the object of interest is first identified before support motion starts, for instance, a bounding box can be placed around the object. It can be assumed that there is no relative movement between the patient support and the object, and the object can be tracked by moving the bounding box in the monitoring image according to the actual support position, i.e. by shifting the bounding box by an offset calculated by mapping the actual support movement, i.e. position, into pixels. The chest, i.e. the region of interest, should then appear to be static within the identified bounding box, at least between subsequent monitoring images with limited support motion.

Preferably, the initial calibration, which can be a real calibration or a virtual calibration, has to be performed only once, for instance, when the camera is fixed to the imaging device and cannot move. In this case it is even possible to perform the calibration only once per design, if tolerances in the manufacturing processes are small enough. It is further preferable that the support movement is limited, for instance, by moving the patient support along rails which are fixed to the imaging device itself. To perform the initial calibration a distinctive object can be used. In an example, an object with a checkerboard pattern is used, because it is commonly used in camera calibration and imaging tracking algorithms, and corner identification algorithms are widely available. A different calibration object could be used as well. During an exemplary embodiment of a calibration method, the patient support is moved to one end and then the calibration object is placed on the patient support. It is advisable to place the calibration object in the center. However, the calibration can also be used based on relative positions. The one-time initial calibration can then be performed by a specific software, namely software for providing the position map. The software running, for instance, on the calibration system as described above, can receive a video stream from the camera and the support position signal in a synchronized manner, so that the support position corresponding to each acquired monitoring image is known. The support is then moved to the other end of the imaging device. Whilst the support moves, the camera can capture the entire motion. Ideally, each support position will be captured by at least one monitoring image. However, it is not necessary to capture all positions. For each monitoring image captured by the camera, for instance, the calibration apparatus as described above can precisely identify the position of the calibration object in the monitoring image, for instance, the pixel value, and link it to the actual support position. In this way a position map can be created.

In actual operating conditions, different patients would lie in slightly different positions and, anyway, different patients may be tall, short, fat, thin, etc. To account for all these differences, a large calibration object may be used. This large calibration object, e.g. a carton box with a checkerboard pattern drawn on it, can then cover all the possible chest positions, i.e. positions of a region of interest, on the patient support accounting for the expected variability in terms of patient's size, weight, orientation, like head first, legs first, etc. In this way several position maps, i.e. a position map mapping more than one calibration position to a support position, can be created at once, e.g. one per corner of the checkerboard. When using the position map, the bounding box can then be moved according to the position map or a combination of position maps that best approximates the actual position of the bounding box in the first monitoring image. Note that only one position map for only one calibration position may be created in simple calibration methods.

In an alternative embodiment, the camera may not be fixed to the medical imaging device, but to the room. In such a case all the procedures described above can be applied similarly, even though the calibration would only be valid as long as the camera is not moved with respect to the medical imaging device.

Using the position map in real examinations can in one embodiment be done in multiple steps. For instance, by identifying a chest area, defining one or multiple bounding boxes containing the area of interest, for instance the chest area, and then, once the boundaries of the areas to be monitored are known and support motion starts, moving the bounding boxes accordingly so that the objects of interest are tracked. Note that the boundaries of the regions of interest can even be represented by single points in the image.

Since the calibration will use only a finite set of positions representing a finite set of likely positions of a region of interest, the method can include performing an interpolation of the positions used in the position map. For example, given an initial position of the chest area, the four nearest neighbors in the position map can be identified. The new position of the area of interest after support motion can then be found by interpolating the new positions of the four nearest neighbors as given by the position map. In another embodiment, the support position is not received as a signal from the control system, but is extracted by the camera system using, for instance, a marker fixed on the support. This marker can be tracked during the one-time calibration and during actual examinations to provide an indication for the support position.

Although in the above embodiments the camera was provided as part of the imaging device or positioned within the imaging device, the camera can also be positioned independent of the imaging device, for instance, in the corner of a room in which the imaging device is placed or on a tripod near the imaging device. Moreover, more than one camera can be provided for providing the monitoring images. For instance, two cameras can be positioned at different sides of the imaging device for monitoring different support positions.

Although in the above embodiments the imaging device was described as a CT imaging device, the imaging device can also be any other medical imaging device in which a patient support is moved during the imaging procedure, like a PET imaging device, an MR imaging device, a SPECT imaging device, etc.

Although in the above described embodiments the patient support was always a patient support on which a patient was lying during the acquisition of the medical image, the patient support can also be configured for a sitting or a standing patient.

Although in the above embodiments the first monitoring image was the image that was firstly provided by the camera before or at the beginning of the imaging procedure, the first monitoring image can also be defined as a monitoring image that was acquired during, at the end, or after the imaging procedure by the camera. Moreover, the second monitoring images can then be defined accordingly, for instance, as monitoring images acquired before the acquisition of the first monitoring image.

Although in the above embodiments only one position map was provided by the position map providing unit, in other embodiments the position map providing unit can be adapted to provide a plurality of position maps. For instance, the position map providing unit can be adapted to provide different position maps for different imaging systems or for different configurations of the imaging systems. Also position maps for different positions and fields of view of the camera, and/or different calibration objects placed at different positions on the patient support can be provided by the position map providing unit. The position map providing unit can then be adapted, for instance, to select one of the provided position maps based on an input of the user, configuration data of the imaging system, information on the patient, the region of interest, etc.

Although in the above embodiments the position map was determined using a real calibration procedure, in other embodiments the position map can be determined during a virtual calibration procedure, i.e. during a calculation of the monitoring positions based on a virtual calibration object, virtual monitoring images and a virtual support, wherein models can be used to simulate the position of the virtual calibration object in the virtual monitoring images to determine the position map.

Other variations to the disclosed embodiments can be understood and effected by those skilled in the art in practicing the claimed invention from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the providing of the monitoring image or the determination of the position of the region of interest in the second monitoring image performed by one or several units or devices can be performed by any other number of units or devices. For instance, these procedures can be carried out by a single device. These procedures and/or the control of the apparatus for monitoring a subject can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention refers to an apparatus for monitoring a subject during an imaging procedure, e.g. CT-imaging. The apparatus comprises a monitoring image providing unit providing a first monitoring image and a second monitoring image acquired at different support positions, a monitoring position providing unit providing a first monitoring position of a region of interest in the first monitoring image, a support position providing unit providing support position data of the support positions, a position map providing unit providing a position map mapping calibration support positions to calibration monitoring positions, and a region of interest position determination unit determining a position of the region of interest in the second monitoring image based on the first monitoring position, the support position data, and the position map. This allows to determine the position of the region of interest accurately and with low computational effort.

The invention claimed is:

1. An apparatus for monitoring a subject during a medical imaging procedure using a medical imaging device, wherein the imaging device comprises a support for supporting the subject and moving the subject during the imaging procedure, the apparatus comprising:
 a memory that stores a plurality of instructions; and
 processor circuitry that couples to the memory and is configured to execute the plurality of instructions to:
  provide monitoring images of the subject comprising a first monitoring image and a second monitoring image of the subject, wherein the first monitoring image is acquired at a first support position and the second monitoring image is acquired at a second support position,
  provide a first monitoring position and shape being indicative of a position and shape of a region of interest in the first monitoring image,
  provide support position data being indicative of the second support position,
  provide a position map for mapping calibration support positions with calibration monitoring positions of a calibration procedure during which calibration monitoring images are acquired at different calibration support positions with a calibration object supported by the support, wherein a calibration monitoring position is indicative of a position of the calibration object in a calibration monitoring image at a respective calibration support position indicated by calibration support position data, and
  determine a position and shape of the region of interest in the second monitoring image based on the first monitoring position and shape, the support position data, and the position map, wherein a change in the shape of the region of interest of the subject is monitored based on the second monitoring image and the position of the region of interest in the second monitoring image.

2. The apparatus according to claim 1, wherein the monitoring images comprise a plurality of second monitoring images acquired at at least one second support position, wherein the processor circuitry is configured to provide support position data for each of the at least one second support position, and determine the position and shape of the region of interest in each of the second monitoring images.

3. The apparatus according to claim 1, wherein the position map maps a plurality of calibration monitoring positions in respect of each calibration support position, each calibration monitoring position being indicative of a position of a different part of a calibration object supported by the support.

4. The apparatus according to claim 3, wherein the processor circuitry is configured to provide the first monitoring position in the first monitoring image based on a first monitoring position received from a user or based on information on where the location of the region of interest is normally to be expected in the first monitoring image.

5. The apparatus according to claim 3, wherein determining the position of the region of interest in the second monitoring image comprises determining a first calibration monitoring position, wherein the first calibration monitoring position corresponds to a calibration monitoring position in the position map that is derived from the first monitoring position in the first monitoring image, and determining the position of the region of interest further based on the first calibration monitoring position.

6. The apparatus according to claim 5, wherein determining the position of the region of interest in the second monitoring image comprises determining at least two calibration monitoring positions that are derived from the first monitoring position as first calibration monitoring positions, wherein the position of the region of interest is then determined further by interpolating between monitoring positions determined in the second monitoring image based on the position map and the first calibration monitoring positions.

7. The apparatus according to claim 1, wherein determining the position of the region of interest in the second monitoring image comprises determining a virtual first support position comprising the result of processing the first monitoring position using the position map and determining the position of the region of interest in the second monitoring image based on the virtual first support position, the support position data, and the position map.

8. The apparatus according to claim 1, wherein the support position data comprises a difference between the first support position and the second support position, and wherein the processor circuitry is configured to determine the position of the region of interest in the second monitoring image based on the first monitoring position, the difference, and the position map.

9. The apparatus according to claim 1, wherein the processor circuitry is configured to provide the support position data based on the first monitoring image and the second monitoring image by identifying the support in the respective images.

10. The apparatus according to claim 1, wherein each monitoring image is acquired by a camera, wherein the field of view of each monitoring image is the same and covers all positions of interest of the region of interest during the medical imaging procedure.

11. A system for acquiring a medical image of a subject during a medical imaging procedure, comprising:
 a medical imaging device for acquiring a medical image, wherein the medical imaging device comprises a support for supporting the subject during the medical imaging procedure;
 a camera for acquiring monitoring images of the subject during the medical imaging procedure; and
 an apparatus comprising:
  a memory that stores a plurality of instructions; and
  processor circuitry that couples to the memory and is configured to execute the plurality of instructions to:

provide monitoring images of the subject comprising a first monitoring image and a second monitoring image of the subject, wherein the first monitoring image is acquired at a first support position and the second monitoring image is acquired at a second support position, provide a first monitoring position and shape being indicative of a position and shape of a region of interest in the first monitoring image, provide support position data being indicative of the second support position, provide a position map for mapping calibration support positions with calibration monitoring positions of a calibration procedure during which calibration monitoring images are acquired at different calibration support positions with a calibration object supported by the support, wherein a calibration monitoring position is indicative of a position of a calibration object in a calibration monitoring image at a respective calibration support position indicated by calibration support position data, and determine a position and shape of the region of interest in the second monitoring image based on the first monitoring position and shape, the support position data, and the position map, wherein a change in the shape of the region of interest of the subject is monitored based on the second monitoring image and the position of the region of interest in the second monitoring image.

12. A method for monitoring a subject during a medical imaging procedure using a medical imaging device, wherein the imaging device comprises a support for supporting the subject and moving the subject during the imaging procedure, the method comprising:

providing monitoring images of a subject comprising a first monitoring image and a second monitoring image of the subject, wherein the first monitoring image is acquired at a first support position and the second monitoring image is acquired at a second support position;

providing a first monitoring position and shape being indicative of a position and shape of a region of interest in the first monitoring image;

providing support position data being indicative of the second support position;

providing a position map for mapping calibration support positions with calibration monitoring positions, wherein a calibration monitoring position is indicative of a position of a calibration object in a monitoring image acquired at a respective calibration support position indicated by calibration support position data; and determining a position and shape of the region of interest in the second monitoring image based on the first monitoring position and shape, the support position data, and the position map, wherein a change in the shape of the region of interest of the subject is monitored based on the second monitoring image and the position of the region of interest in the second monitoring image.

\* \* \* \* \*